United States Patent
Hilfinger et al.

[19]
[11] Patent Number: 5,842,244
[45] Date of Patent: Dec. 1, 1998

[54] BRUSH SECTION FOR AN ELECTRIC TOOTHBRUSH

[75] Inventors: Peter Hilfinger, Bad Homburg; Gerhard Kressner, Altenstadt; Georges Driesen, Weilrod; Karl Herzog, Frankfurt, all of Germany

[73] Assignee: Braun Aktiengesellschaft, Frankfurt, Germany

[21] Appl. No.: 826,557

[22] Filed: Apr. 4, 1997

Related U.S. Application Data

[63] Continuation of PCT/EP95/03256 Aug. 16, 1995.

[30] Foreign Application Priority Data

Oct. 29, 1994 [DE] Germany .................. 44 38 731.8

[51] Int. Cl.6 .................. A46B 13/02; A61C 17/34
[52] U.S. Cl. .................. 15/22.1; 15/28
[58] Field of Search .................. 15/22.1, 28, 29

[56] References Cited

U.S. PATENT DOCUMENTS

| | | | |
|---|---|---|---|
| 3,984,890 | 10/1976 | Collis | 15/22.1 |
| 4,223,417 | 9/1980 | Solow | 15/22.1 |
| 4,320,774 | 3/1982 | Rogers | 15/22.1 |
| 5,226,206 | 7/1993 | Davidovitz et al. | 15/22.1 |

FOREIGN PATENT DOCUMENTS

| | | |
|---|---|---|
| 191122 | 8/1957 | Austria ........... 15/22.1 |
| 259 648 | 3/1988 | European Pat. Off. . |
| 36 30 499 | 3/1988 | Germany . |
| 39 37 850 | 5/1991 | Germany . |
| 92 00 807.0 | 7/1993 | Germany . |
| 91/03187 | 3/1991 | WIPO . |
| 91/13570 | 9/1991 | WIPO . |

*Primary Examiner*—Mark Spisich
*Attorney, Agent, or Firm*—Fish & Richardson P.C.

[57] ABSTRACT

A brush section for an electric toothbrush includes a driver, a mounting tube which receives the driver, where the driver is arranged in the direction of a longitudinal axis defined by the mounting tube, a first bristle carrier mounted for rotation about a first brush axis, a second bristle carrier mounted for rotation about a second brush axis, and a mechanism to effect coupling engagement of the driver with the first and second bristle carriers. A motion of the driver effects a rotary motion of the first bristle carrier about the first brush axis and the second bristle carrier about the second brush axis. The first and second brush axes define an approximately right angle therebetween.

23 Claims, 10 Drawing Sheets

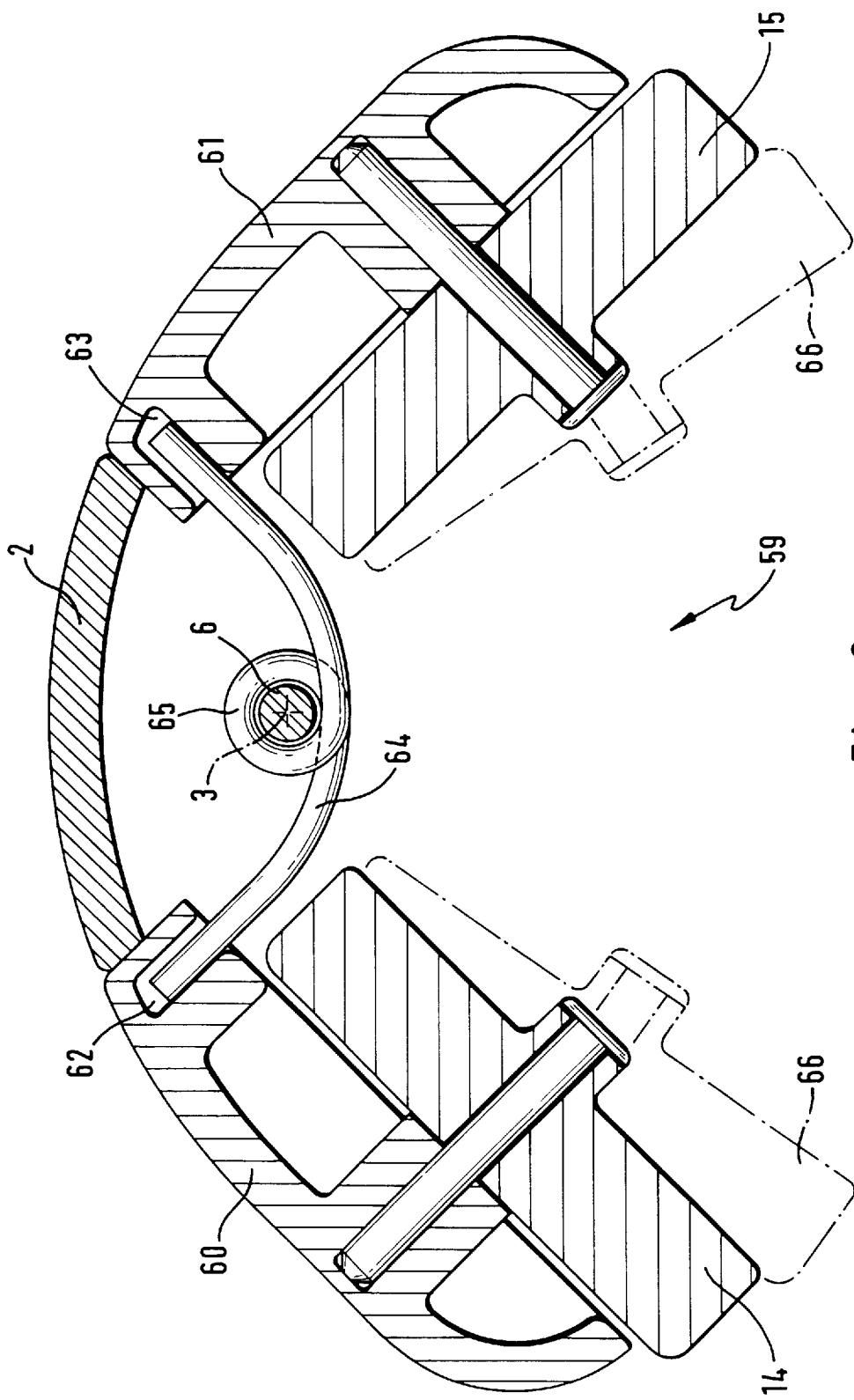

BRUSH SECTION FOR AN ELECTRIC TOOTHBRUSH

CROSS REFERENCE TO RELATED APPLICATION

This application is a continuation of PCT/EP95/03256, filed 16 Aug. 1995.

BACKGROUND OF THE INVENTION

This invention relates very generally to an electric toothbrush and particularly to a brush section for an electric toothbrush.

A brush section of this type is known from International Patent Application WO 91/13570 (PCT/US90/02825). In this specification, an electric toothbrush is described which has a handle section from which a driving rod projects outwardly. The handle section receives in its interior electric drive means with the aid of which an oscillatory motion in the direction of its longitudinal axis can be imparted to the driving rod. A brush section extending in the direction of the longitudinal axis and having a mounting tube with two bristle carriers arranged at its end is adapted to be push-fitted onto the handle section and the driving rod. The mounting tube accommodates therein a rod which, when push-fitted, is coupled to the driving rod. The two bristle carriers are mounted for rotation about brush axes disposed transversely to the longitudinal axis, so that the bristles extending from the two bristle carriers are approximately parallel, facing each other. By means of coupling means arranged between the two bristle carriers and thus in the area of the bristles, the oscillatory longitudinal motion transmitted from the driving rod to the rod of the brush section is deflected, such that in operation of the electric toothbrush the two bristle carriers perform an oscillatory rotational motion about their brush axes. When a user introduces the teeth to be cleaned between the two bristle carriers, cleaning of the teeth may be effected by means of the bristles extending from the two bristle carriers. However, the coupling means arranged between the bristle carriers and thus in the area of the bristles have proven to be an impediment to the cleaning action.

SUMMARY OF THE INVENTION

It is an object of the present invention to devise a brush section for an electric toothbrush with which an improved cleaning action is achievable for its user.

According to the present invention, this object is accomplished in a brush section which includes a first bristle carrier mounted for rotation about a first brush axis, and a second bristle carrier mounted for rotation about a second brush axis, where the first and second brush axes define an approximately right angle therebetween.

By arranging the two brush axes in a plane which is preferably, but not indispensably at about right angles to the longitudinal axis, and by providing an about right angle between the two brush axes, it is accomplished that the coupling means need no longer be arranged between the two bristle carriers and thus in the area of the bristles, but rather, that the coupling means may be arranged on the side of the bristle carriers remote from the bristles. The tooth cleaning action can no longer be impeded by any coupling means, resulting in a substantially simplified and accordingly improved tooth cleaning action on the user's part. It will be understood, of course, that the brush axes may also be arranged at an acute or obtuse angle to the longitudinal axis. The arrangement of the brushes as disclosed in the invention also ensures that the surfaces of a tooth to be cleaned are essentially fully covered or swept by the brushes or bristles without involving the need for changing the position of the brush relative to the tooth.

In an advantageous feature of the present invention, the oscillatory rotational motion of the driving rod is transmitted to the two bristle carriers by means of two connecting rods. This provides a simple and thus low-cost structure of the coupling means. Also, this structure affords quick and easy assembly of the brush section.

In this arrangement, it is particularly advantageous if the two connecting rods are connected off-center with the shaft and with the two bristle carriers. This enables a simple and a reliable transmission of the oscillatory rotational motion from the shaft to the two bristle carriers.

In a suitable further aspect, pins associated with corresponding eyes of the connecting rods extend from the shaft and from the two bristle carriers. In this arrangement, the pins are a press-fit within the shaft and the bristle carriers, for example. When the shaft is set in an oscillatory rotational motion about its longitudinal axis, this rotational motion is transmitted to the respective bristle carrier via the pin fitted in the shaft off-center, the connecting rod seated on the pin, and the pins fitted in the bristle carriers off-center. Overall, the further aspect described presents a simple and reliable structure enabling further the brush section to be manufactured quickly and economically.

In an advantageous feature of the present invention, the oscillatory longitudinal motion of the rod is transmitted to the two bristle carriers by means of two connecting rods. This presents a further possibility for a simple and accordingly economical coupling means structure.

It is of a particular advantage in this arrangement if the two connecting rods have one end connected with the rod and the other end connected off-center with a respective one of the two bristle carriers.

In a suitable further aspect, respective pins associated with corresponding eyes of the connecting rods extend from the rod and from the two bristle carriers. In this arrangement, the pins are a press-fit within the rod and the bristle carriers, for example. When the rod is set in an oscillatory longitudinal motion, this motion is transmitted to the associated bristle carriers via the pin fitted in the rod, the connecting rods seated on the pin, and the pins fitted in the bristle carriers off-center. Overall, this presents a simple and reliable structure enabling the brush section to be manufactured economically.

In an advantageous feature of the present invention, the eyes and the pins have sufficient relative clearance to enable a spatial movement of the connecting rods. The joints formed by the pins and the eyes of the connecting rods seated on the pins thus have degrees of freedom similar to a ball-and-socket joint, yet they are substantially simpler and thus more economical with regard to their structure and manufacture.

In another advantageous feature of the present invention, the two connecting rods are fabricated from a bent piece of round metal. This has the advantage that the connecting rods have sufficient stability to transmit the motions of the shaft or the rod to the bristle carriers, while at the same time the at least slightly resilient property of the round metal imparts a further degree of freedom to the whole structure which further aids in facilitating and thus improving the transmission of motion from the shaft or the rod to the bristle carriers.

In an advantageous feature of the present invention, the oscillatory longitudinal motion of the rod is transmitted to the two bristle carriers by means of a transverse rod. This presents a further possibility for a straightforward and thus economical coupling means structure.

In a suitable further aspect, respective pins associated with mating slots in the transverse rod extend from the two bristle carriers. When the rod is set in an oscillatory longitudinal motion, this motion is transmitted via the transverse rod fixedly connected with the rod and via the pin passed through the slot to the associated bristle carrier. Overall, this presents a simple and reliable structure affording economy of manufacture of the brush section.

In a particularly advantageous feature of the invention, which may also involve an independent invention, the two bristle carriers are affixed to arms arranged so as to be pivotal relative to each other. As a result, the two bristle carriers can be urged away and towards each other. In this manner, the angle at which the bristles extending from the two bristle carriers are arranged relative to each other can be varied and hence adapted optimally to the thickness of the teeth to be cleaned. As a result, both incisors and molars can be cleaned uniformly.

In an advantageous further aspect, the angle at which the bristles extending from the two bristle carriers are arranged relative to each other is varied by a spring. If a person utilizes an excessive force to position the two bristle carriers against the tooth surfaces to be cleaned, the bristle carriers will be urged apart and hence the engagement force will be reduced. Conversely, if the force is too low, the spring will urge the two bristle carriers together again in the direction of their initial position, which corresponds to an increase in the engagement force. Overall, therefore, the spring operates to produce in wide areas an approximately constant bristle engagement force on the tooth surfaces to be cleaned. Conveniently, in the initial position the two bristle carriers define between them a minimum angle, in particular an angle smaller than 90 degrees, for example, 80 degrees, approximately. In urged apart condition, the angle defined between the two bristle carriers is suitably greater than 90 degrees, in particular 100 degrees, approximately.

In an advantageous further aspect, the shaft and the two arms with the bristle carriers are mounted on the same bearing pin. If soiling of this bearing occurs due to toothpaste residues or the like, such contaminants which adversely affect the pivotability of the two arms holding the bristle carriers and thus of the two bristle carriers are expelled by the movement of the shaft. Full functional reliability of the bristle carriers is thus ensured, and the user is in a position to obtain consistently good cleaning results with the brush section.

In an advantageous feature of the present invention, which may also involve an independent invention, the bristle carriers are of an oval configuration in at least one direction. This enables a better cleaning operation to be accomplished.

It is particularly suitable to arrange the oval configurations of the two bristle carriers so as to be facing each other. This has the advantage that a higher number of bristles is present in the overlap area formed by the facing bristle carriers. As a result, the cleaning action of the brush section is improved still further.

In another advantageous feature of the present invention which may also involve an independent invention, the bristles extending from each of the two bristle carriers define between them an included angle. As a result, the bristles of each bristle carrier are optimally conformed to the shape of the teeth to be cleaned. Extending from the respective bristle carrier at various angles, the bristles also engage the tooth surfaces at various angles. In particular the chewing surfaces of the teeth are cleaned more uniformly and thus more thoroughly by the various bristles of the brush section.

It is particularly suitable in this arrangement if the facing bristles of the two bristle carriers define an acute angle with the associated brush axis, and if the remaining bristles are aligned approximately parallel to the brush axis.

In another advantageous feature of the present invention which may also involve an independent invention, the bristles extending from each of the two bristle carriers differ in length. This has equally the effect that the tooth surfaces to be cleaned, in particular the curvatures and chewing surfaces of the teeth to be cleaned, are better reached by the different lengths of bristles, thus enhancing the cleaning action of the brush section of the invention.

It is particularly convenient in this arrangement if the length of the bristles increases progressively as the relative distance of facing bristles becomes greater.

Further features, advantages and application possibilities of the present invention will become apparent from the subsequent description of embodiments illustrated in more detail in the accompanying drawings. It will be understood that any single feature and any combination of single features described and/or represented by illustration form the subject-matter of the present invention, irrespective of their summary in the claims and their back-reference.

BRIEF DESCRIPTION OF THE DRAWINGS

FIG. 2a is a schematic cross-sectional view of the brush section of FIG. 1, taken along the plane 2a—2a of FIG. 1;

FIG. 2b is a schematic sectional view of the brush section of FIG. 1, taken along the plane 2b—2b of FIG. 2a;

FIG. 2c is a schematic sectional view of the brush section of FIG. 1, taken along the plane 2c—2c of FIG. 2a;

FIG. 6 is a schematic cross sectional view of a brush section for an electric toothbrush utilizing a fourth embodiment, taken along a plane corresponding to the plane 2a—2a of FIG. 1;

DETAILED DESCRIPTION

Figure 1:
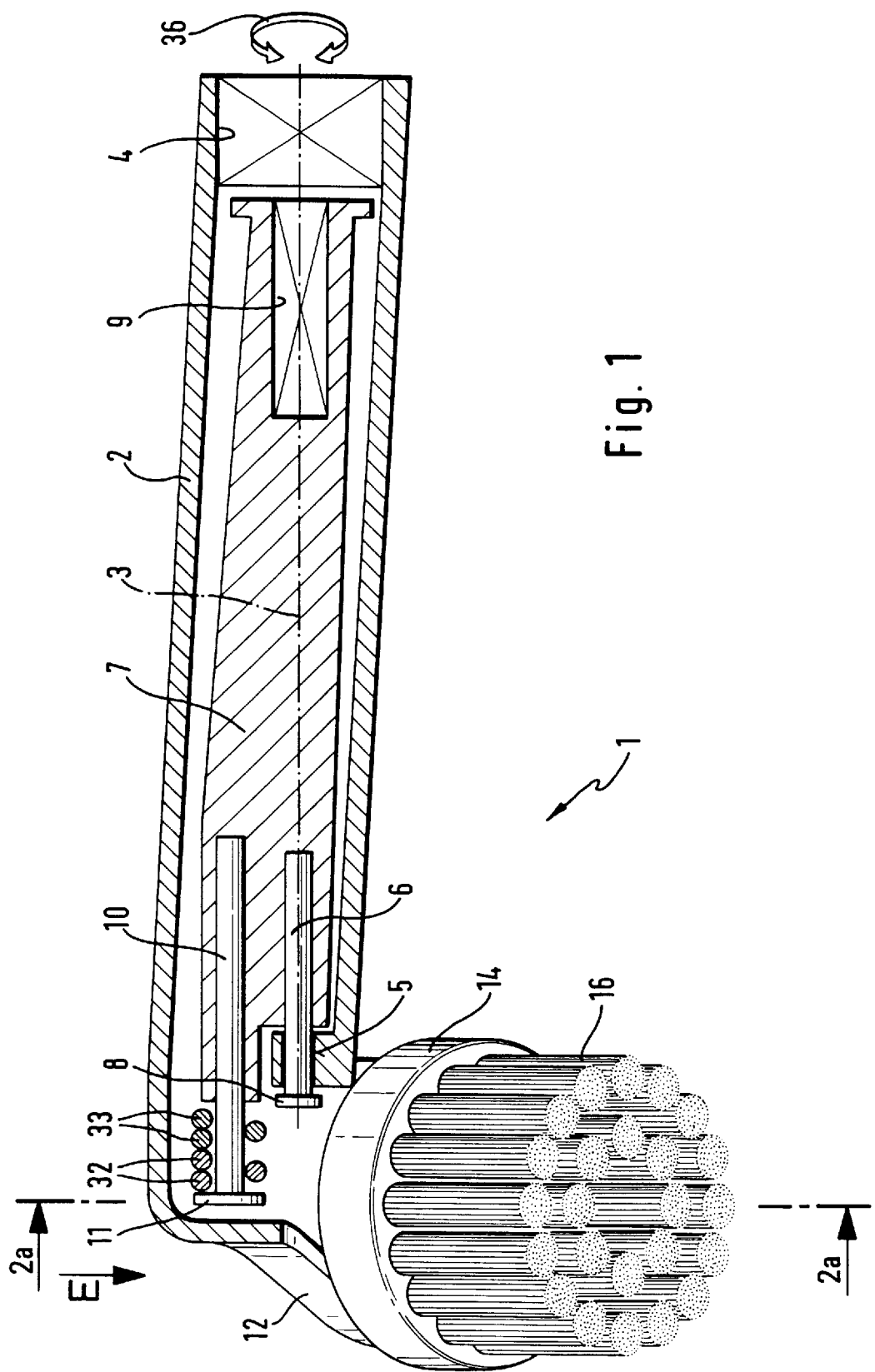
FIG. 1 is a schematic longitudinal sectional view, taken along the plane 1—1 of FIG. 2a, of a brush section for an electric toothbrush utilizing a first embodiment of the invention.
Figure 2:
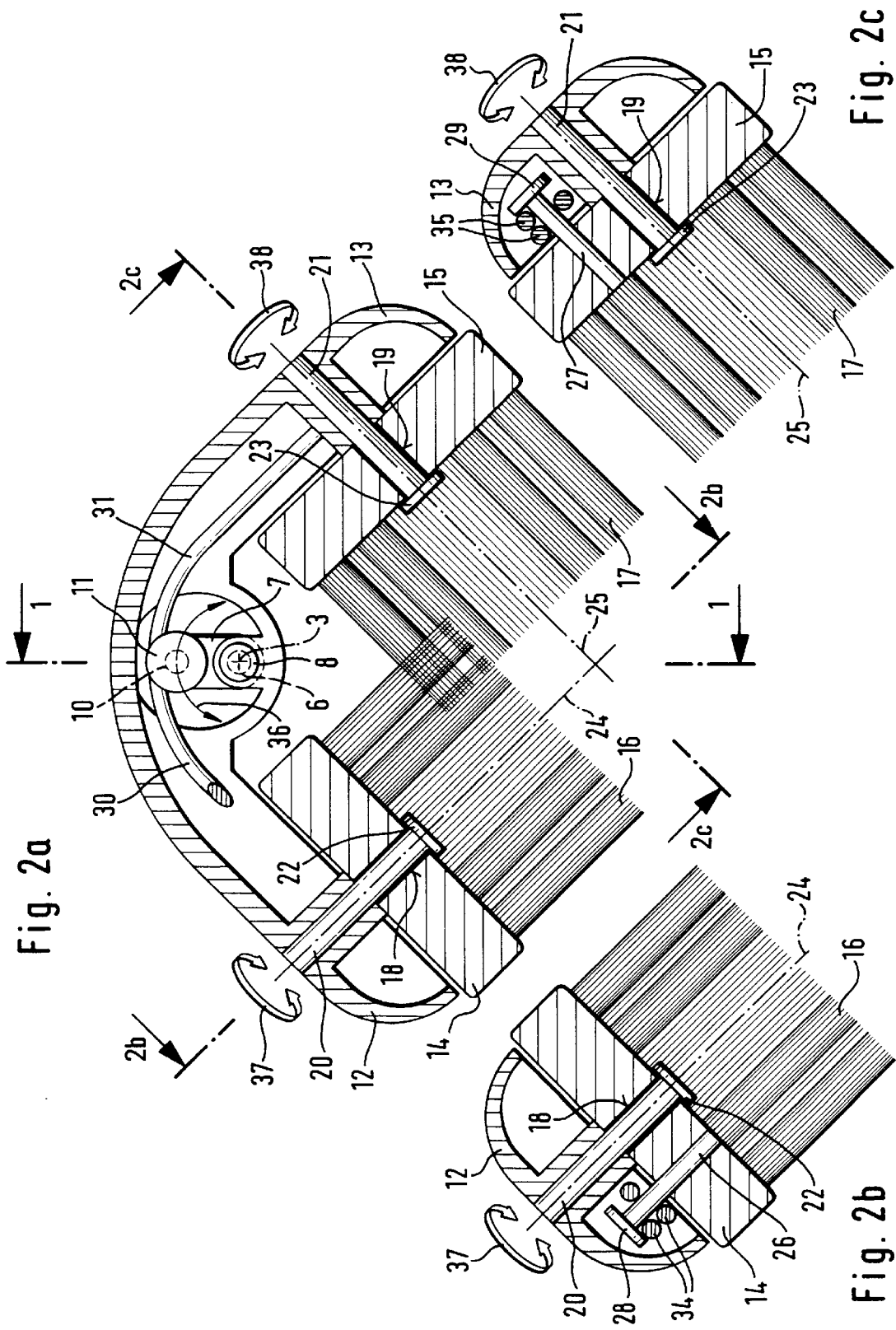
Figure 3:
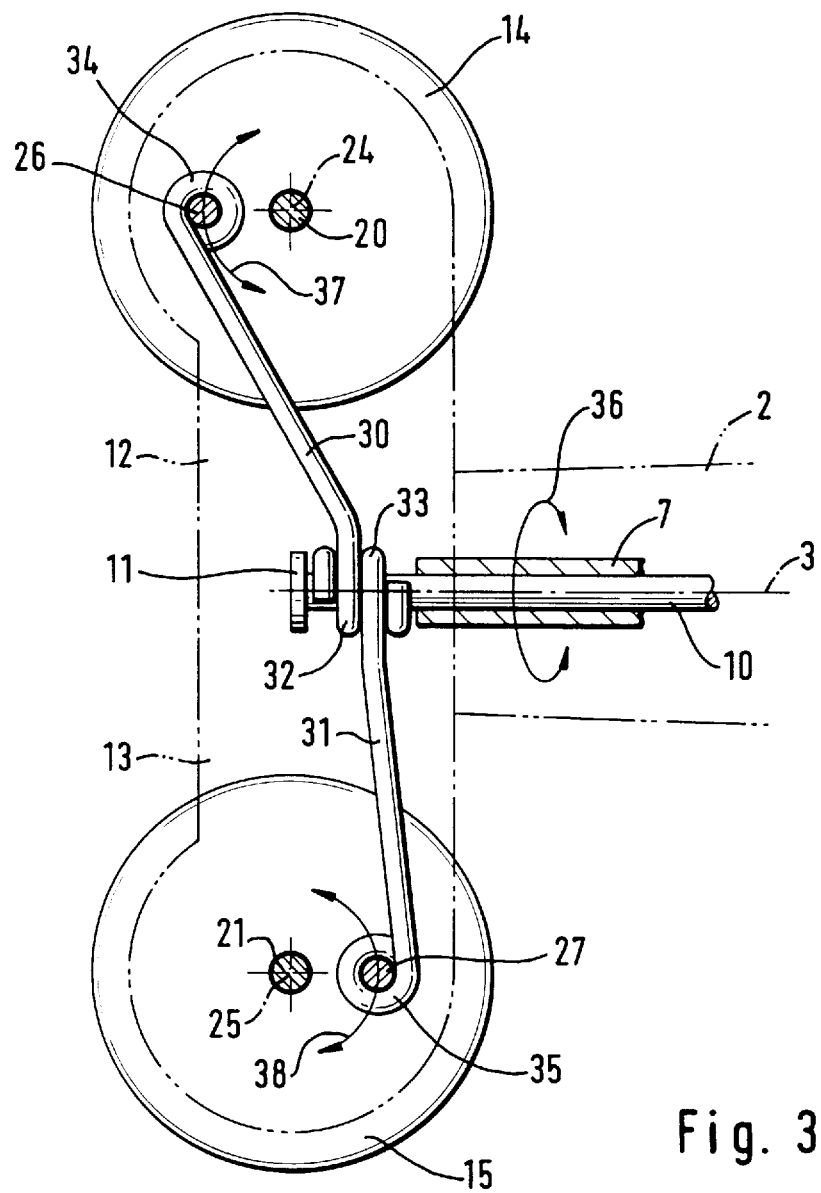
FIG. 3 is a schematic unfolded view of the brush section of FIG. 1, as seen looking in the direction E of FIG. 1.

The brush sections described in the following with reference to FIGS. 1 to 9b are suited to operate in conjunction with an electric toothbrush of the type disclosed in German Offenlegungsschrift DE 39 37 850 A1 which is hereby incorporated in the disclosure content of the present patent application by express reference. It will be appreciated that the oscillatory rotational motion of the drive shaft of the electric toothbrush as set forth in the Offenlegungsschrift referred to may be replaced by an oscillatory longitudinal motion of a driving rod. It is pointed out by express reference that the present invention may be implemented on the basis of either approach.

The electric toothbrush disclosed in German Offenlegungsschrift DE 39 37 850 A1 includes a handle section from which a drive shaft projects outwardly. The handle section accommodates in its interior electric drive means imparting an oscillatory rotational motion to the drive shaft about its longitudinal axis when activated. The drive shaft and that end of the handle section from which the drive shaft projects have their outer surfaces contoured for push-fitting engagement with a brush section and for transmission of the rotary motion produced.

FIGS. 1 to 4 illustrate a brush section 1 which may be push-fitted onto the handle section and the drive shaft of the electric toothbrush referred to above. The brush section 1 includes a mounting tube 2 extending approximately in the direction of a longitudinal axis 3. At its free end close to the handle section, the mounting tube 2 has an inside contour 4 that is complementary with the outside contour of the handle section. In this manner, the brush section 1 can be push-fitted onto the handle section in a manner preventing relative rotation.

At its end remote from the handle section within an inwardly extending projection, the mounting tube 2 has a bore 5 in which a bearing pin 6 is mounted for rotation. The bearing pin 6 is arranged in the longitudinal axis 3. The bearing pin 6 has its one end firmly press-fitted into the end of a shaft 7. The other end of the bearing pin 6 is provided with a disk 8 at the end of the bore 5 remote from the shaft 7. The shaft 7 is thus arranged in the longitudinal axis 3 of the mounting tube 2, the disk 8 preventing the shaft from being displaced in the direction of the longitudinal axis 3.

The shaft 7 extends over nearly the full length of the mounting tube 2 and is preferably made of plastic. The shaft 7 has at its free end close to the handle section an inside contour 9 complementary with the outside contour of the drive shaft projecting outwardly from the handle section. This enables the drive shaft to be coupled to the shaft 7 in a manner preventing relative rotation.

The inside and outside contours 4, 9 may be of a square, stellate or similar configuration when viewed in cross section, which are conformed to each other such as to enable a user to push and pull the brush section 1 onto and, respectively, off the handle section with ease, while at the same time a secure seat of the brush section 1 on the handle section is ensured.

Spaced from the longitudinal axis 3, a pin 10 is a firm press-fit within the forward end of the shaft 7. The pin 10 is arranged parallel to the longitudinal axis 3 and thus to the bearing pin 6, protruding in length beyond the bearing pin 6. A disk 11 is provided at the free end of the pin 10.

In the area of the pin 10, the mounting tube 2 continues in two arms 12, 13 extending at approximately right angles from the mounting tube 2 and defining between them an approximately right angle. At the free ends of the arms 12, 13, a respective bristle carrier 14, 15 is mounted for rotation. The two bristle carriers 14, 15 are of a disk-shaped configuration. Respective bristles 16, 17 extend from the sides of the bristle carriers 14, 15 facing away from the arms 12, 13, the bristles being at approximately right angles to the bristle carriers 14, 15.

For rotatable mounting, each of the two bristle carriers 14, 15 has an approximately central bore 18, 19 arranged approximately parallel to the bristles 16, 17 and hence approximately transversely to the bristle carriers 14, 15. A respective bearing pin 20, 21 is a firm press-fit within the two arms 12, 13. These two bearing pins 20, 21 are each at right angles to the associated arm 12, 13, forming with one another an approximately right angle. The two bearing pins 20, 21 are passed through the respective bore 18, 19 of the associated bristle carrier 14, 15. The two bearing pins 20, 21 have at their free ends a respective disk 22, 23. The two bristle carriers 14, 15 are thus mounted for rotation about the brush axes 24, 25 formed by the two bearing pins 20, 21.

Spaced from the two brush axes 24, 25, a respective pin 26, 27 is a firm press-fit within each of the two bristle carriers 14, 15. The pins 26, 27 are arranged approximately parallel to the associated brush axes 24, 25, protruding beyond the bristle carriers 14, 15 on the side facing away from the bristles 16, 17. The free ends of the two pins 26, 27 are provided with respective disks 28, 29.

Figure 4A:
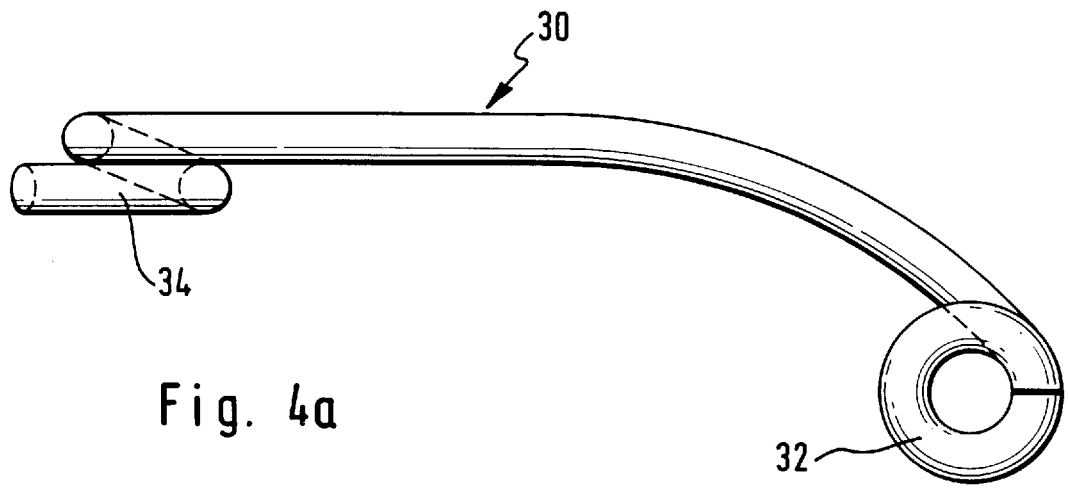
FIG. 4 is a schematic view of a connecting rod for the brush section of FIG. 1 as seen looking in two orthogonal directions.
Figure 4B:
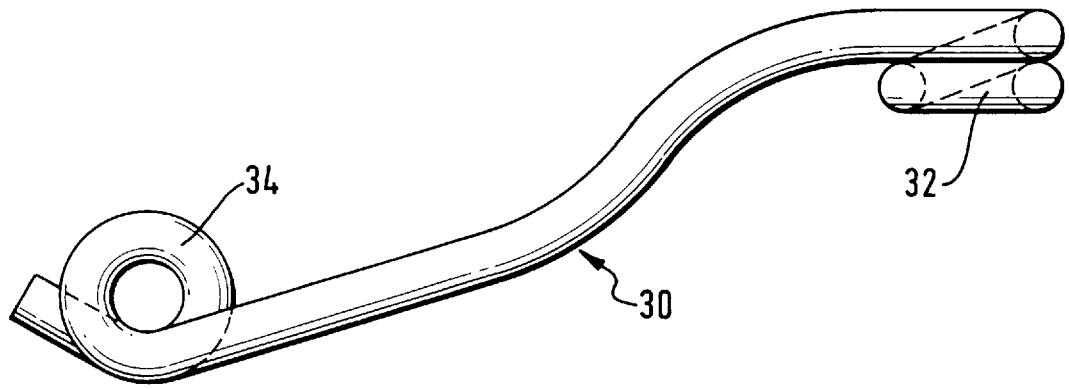

The pin 10 push-fitted into the shaft 7 and the pins 26, 27 push-fitted into the bristle carriers 14, 15 are coupled to each other by means of two connecting rods 30, 31. The connecting rods 30, 31 are fabricated from a bent piece of round metal. By way of example, reference is made preferably to FIG. 4 showing the spatial configuration of the connecting rod 30 in greater detail.

Each of the connecting rods 30, 31 has at its free ends a respective eye 32, 33, 34, 35. These eyes 32, 33, 34, 35 serve for seating engagement of the connecting rods 30, 31 with the pins 10, 26, 27. In this arrangement, the pin 10 protruding from the shaft 7 receives the eyes 32, 33 of the two connecting rods 30, 31, while the pin 26 extending from the bristle carrier 14 is passed through the eye 34 of the connecting rod 30, and the pin 27 extending from the bristle carrier 15 is passed through the eye 35 of the connecting rod 31. The pins 10, 26, 27 and the eyes 32, 33, 34, 35 have such high relative clearance as to enable relative spatial movement.

In the brush section 1 described with reference to FIGS. 1 to 4, the drive shaft extending from the handle section of the electric toothbrush performs an oscillatory rotational motion. When, with the brush section 1 fitted and the electric toothbrush activated, the shaft 7 is equally set in oscillatory rotational motion 36 about the longitudinal axis 3, the pin 10 executes an oscillatory pivotal motion about the longitudinal axis 3 on the arc of a circle. This pivotal motion is transmitted by means of the two connecting rods 30, 31 to the pins 26, 27 which in turn execute each an oscillatory pivotal motion on the arc of a circle about their respective brush axes 24, 25. This pivotal motion involves at the same time an oscillatory rotational motion 37, 38 of the bristle carriers 14, 15 about the brush axes 24, 25. In consequence, also the free ends of the bristles 16, 17 execute the oscillatory rotational motion 37, 38 on the tooth surfaces to be cleaned.

Figure 5A:
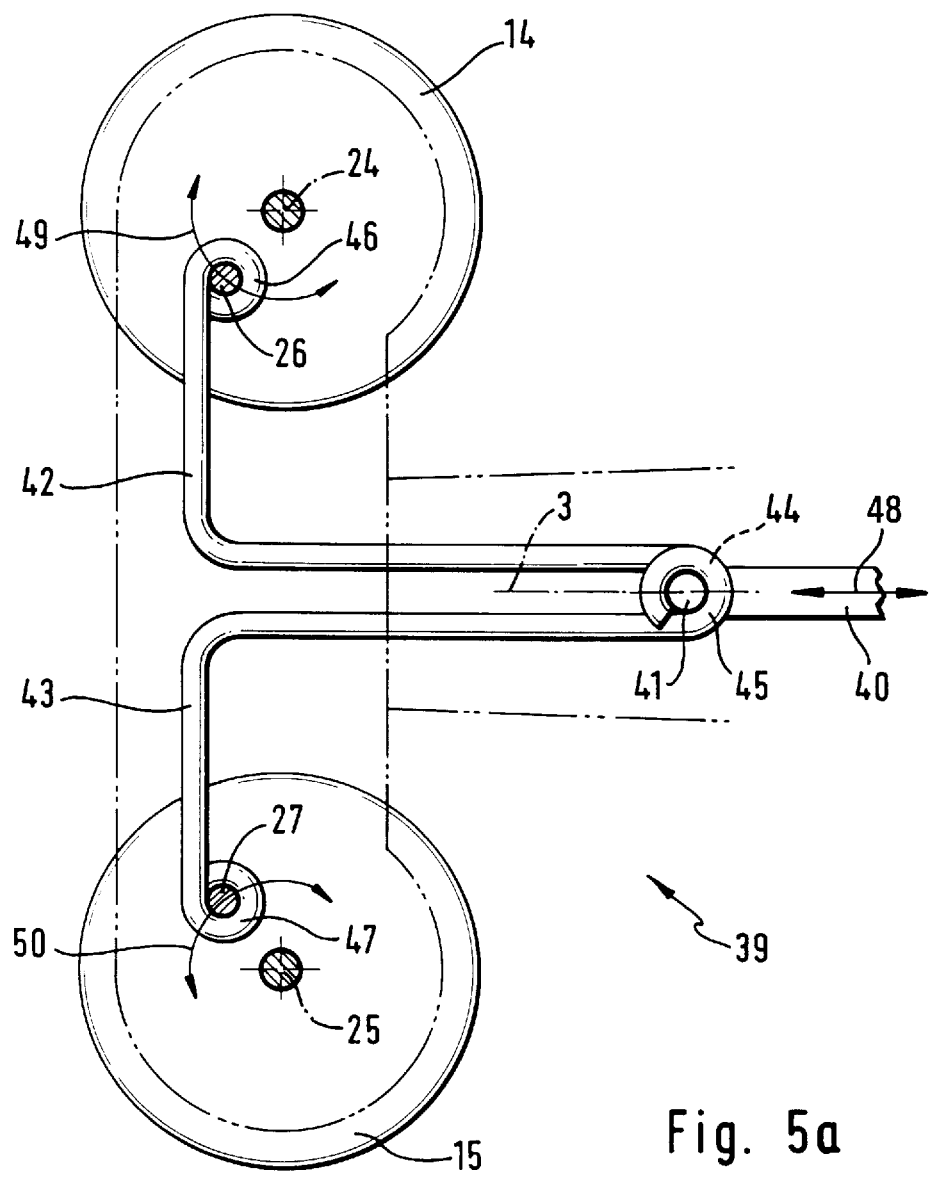
FIG. 5a is a schematic unfolded view of a brush section for an electric toothbrush utilizing a second embodiment, as seen looking in a direction corresponding to the direction E of FIG. 1.

FIG. 5a illustrates a brush section 39 which includes a rod 40 arranged displaceably in the direction of the longitudinal axis 3. At its free end a pin 41 is a firm press-fit within the rod 40. The pin 41 is disposed approximately transversely to the longitudinal axis 3. The pin 41 and the two pins 26, 27 press-fitted into the bristle carriers 14, 15 are coupled to each other by means of two connecting rods 42, 43. The two connecting rods 42, 43 have at their free ends two eyes 44, 45 and, respectively 46, 47 which are in seating engagement with the respective pins 41, 26, 27. In this embodiment, the eyes 44, 45 of the two connecting rods 42, 43 are seated on the pin 41, while the pin 26 is passed through the eye 46 of the connecting rod 42, and the pin 27 is passed through the eye 47 of the connecting rod 43. Owing to the bent configuration of the connecting rods 42, 43, the forward end of the mounting tube 2 and the arms 12, 13 are of slim shape.

In the brush section 39 described with reference to FIG. 5a, the driving rod projecting from the handle section of the electric toothbrush executes an oscillatory longitudinal motion. When the rod 40 is thereby caused to perform equally an oscillatory longitudinal motion 48 in the direction of the longitudinal axis 3, the pin 41 performs the same longitudinal motion 48. The connecting rods 42, 43 operate to transmit this longitudinal motion 48 to the pins 26, 27 causing the pins 26, 27 to pivot about the brush axes 24, 25. This pivotal motion involves at the same time a rotary motion 49, 50 of the bristle carriers 14, 15 about the brush axis 24, 25. As a result, also the free ends of the bristles 16, 17 execute the oscillatory rotational motion 49, 50 on the tooth surfaces to be cleaned.

Figure 5B:
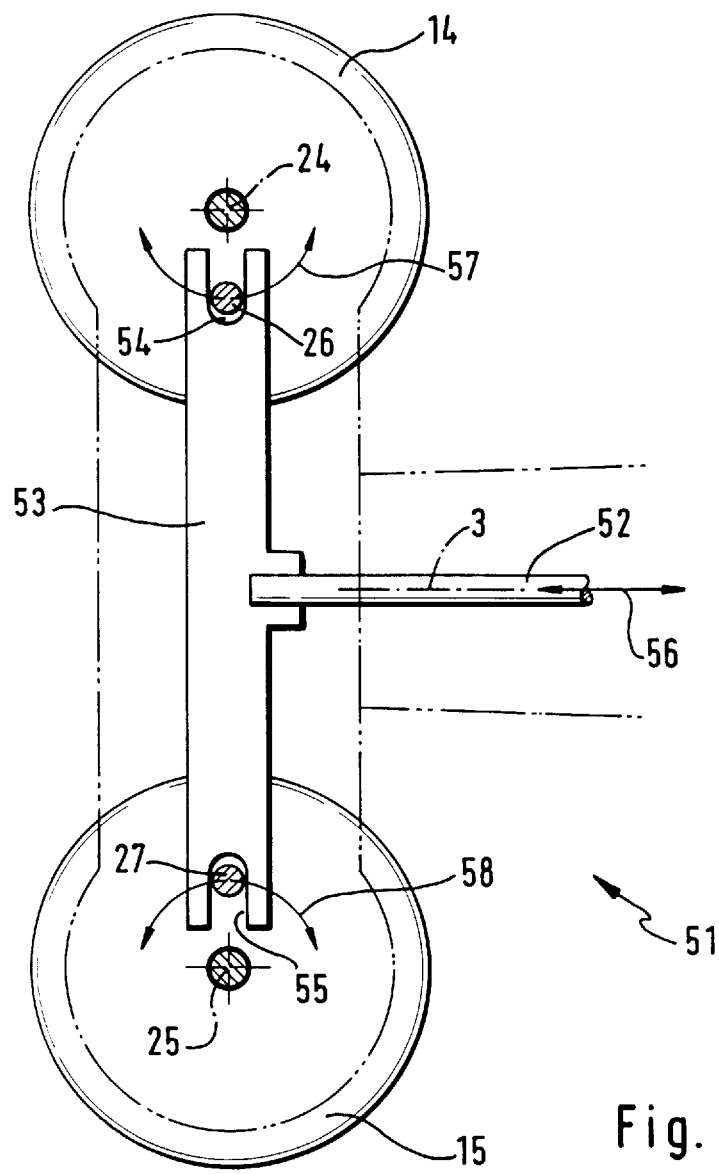
FIG. 5b is a schematic unfolded view of a brush section for an electric toothbrush utilizing a third embodiment, as seen looking in a direction corresponding to the direction E of FIG. 1.

FIG. 5b illustrates a brush section 51 having a rod 52 arranged displaceably in the direction of the longitudinal axis 3. At its free end the rod 52 is fixedly connected with a transverse rod 53. The transverse rod 53 is disposed at approximately right angles to the longitudinal axis 3, extending into the area of the two bristle carriers 14, 15. At each of its free ends the transverse rod has a slot 54, 55 through which the pins 26, 27 extending from the bristle carriers are passed. The pins 26, 27 are movable to and fro within the slots 54, 55.

In the brush section 51 described with reference to FIG. 5b, the driving rod projecting from the handle section of the electric toothbrush executes an oscillatory longitudinal motion. When the rod 52 is thereby caused to perform equally an oscillatory longitudinal motion 56 in the direction of the longitudinal axis 3, the transverse rod 53 performs the same longitudinal motion 56. In consequence, the pins 26, 27 passed through the slots 54, 55 are caused to follow the movement of the transverse rod 53. The pins 26, 27 thereby execute an oscillatory pivotal motion on the arc of a circle about their respective brush axes 24, 25. This pivotal motion involves at the same time an oscillatory rotational motion 57, 58 of the bristle carriers 14, 15 about the brush axes 24, 25. As a result, also the free ends of the bristles 16, 17 execute the oscillatory rotational motion 57, 58 on the tooth surfaces to be cleaned.

In the brush sections described in the following with reference to FIGS. 6 to 9b, either the shaft may execute an oscillatory rotational motion or the rod may execute an oscillatory longitudinal motion, as explained in the foregoing with reference to FIGS. 1 to 4 and FIGS. 5a and 5b. It is pointed out by express reference that the subsequent explanations can be implemented in either approach.

Moreover, it is pointed out by express reference that the features described in the following may each involve an invention in its own right, that is, independently of each other and also independently of the two drive possibilities described.

FIG. 6 shows a brush section 59 having two arms 60, 61 which are connected neither with the mounting tube 2 nor with each other. The two arms 60, 61 extend from the mounting tube 2 at approximately right angles, defining between them an approximately right angle. Each of the two arms 60, 61 is mounted for pivotal motion on the bearing pin 6.

In the region close to the mounting tube 2, each of the two arms 60, 61 has a hole 62, 63 that is open towards the bristle carriers 14, 15 mounted on the arms 60, 61. A metallic spring 64 has its free ends inserted in the two holes 62, 63. Approximately in its center the spring 64 has an eye 65 through which the bearing pin 6 extends.

The two arms 60, 61 are thus pivotally mounted about the bearing pin 6 and hence about the longitudinal axis 3. The force exerted by the spring 64 on the two arms 60, 61 is such as to urge the two arms 60, 61 together in the direction of an initial position 66.

The brush section 59 illustrated in FIG. 6 includes stops limiting the pivotal range of the two arms 60, 61 in a minimum and a maximum direction. The minimum angle which the two arms 60, 61 may define between them is preferably 80 degrees, approximately. The maximum possible angle between the two arms 60, 61 is preferably 90 to 100 degrees, approximately. The spring 64 is biased such as to urge the two arms 60, 61 together in the direction of the minimum angle.

Figure 7:
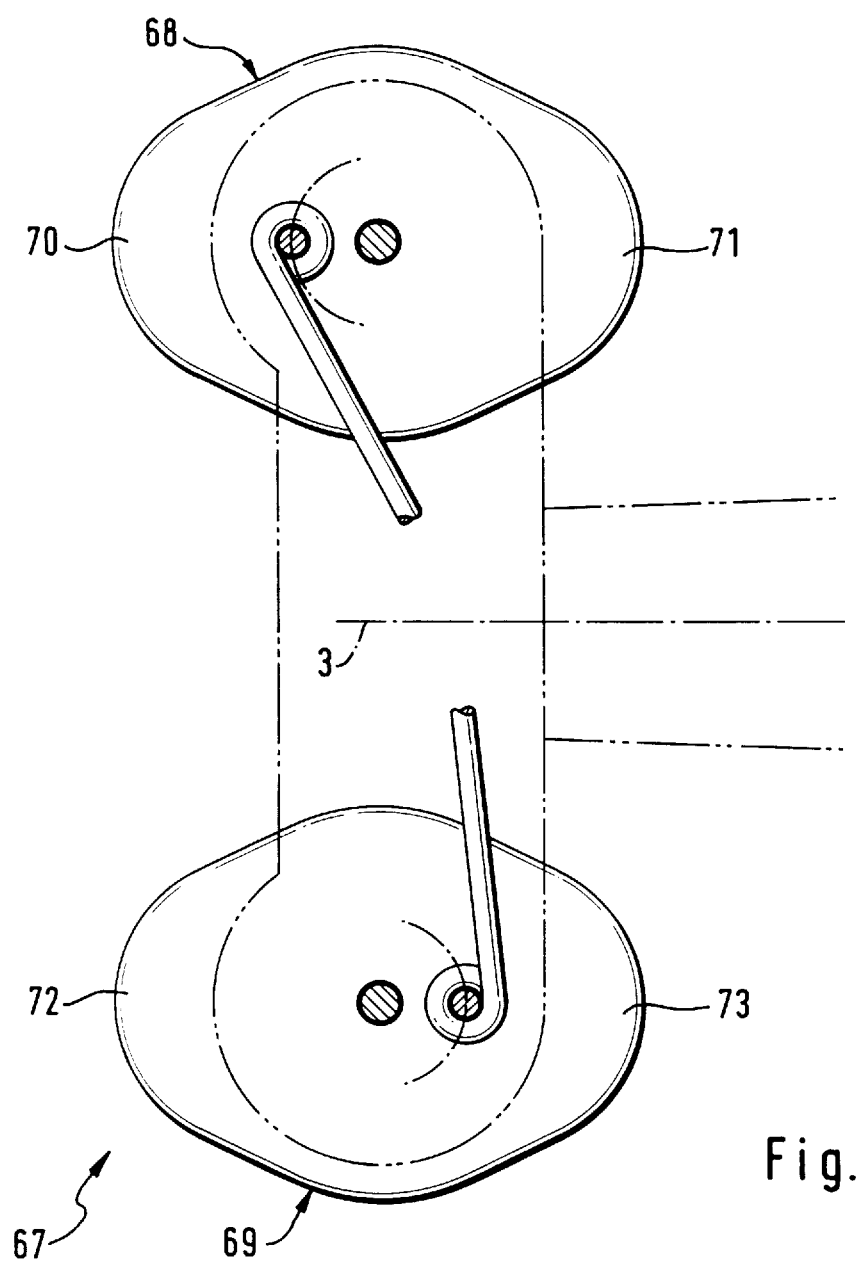
FIG. 7 is a schematic unfolded view of a brush section for an electric toothbrush utilizing a fifth embodiment, as seen looking in a direction corresponding to the direction E of FIG. 1.

FIG. 7 shows a brush section 67 having two bristle carriers 68, 69 which are each of an oval configuration. Each of the two bristle carriers 68, 69 has in the direction of the longitudinal axis 3 two oval bulges 70, 71 and, respectively, 72, 73. The two bristle carriers 68, 69 thus possess a maximum and a minimum diameter which are each arranged approximately parallel to one another.

Figure 8A:
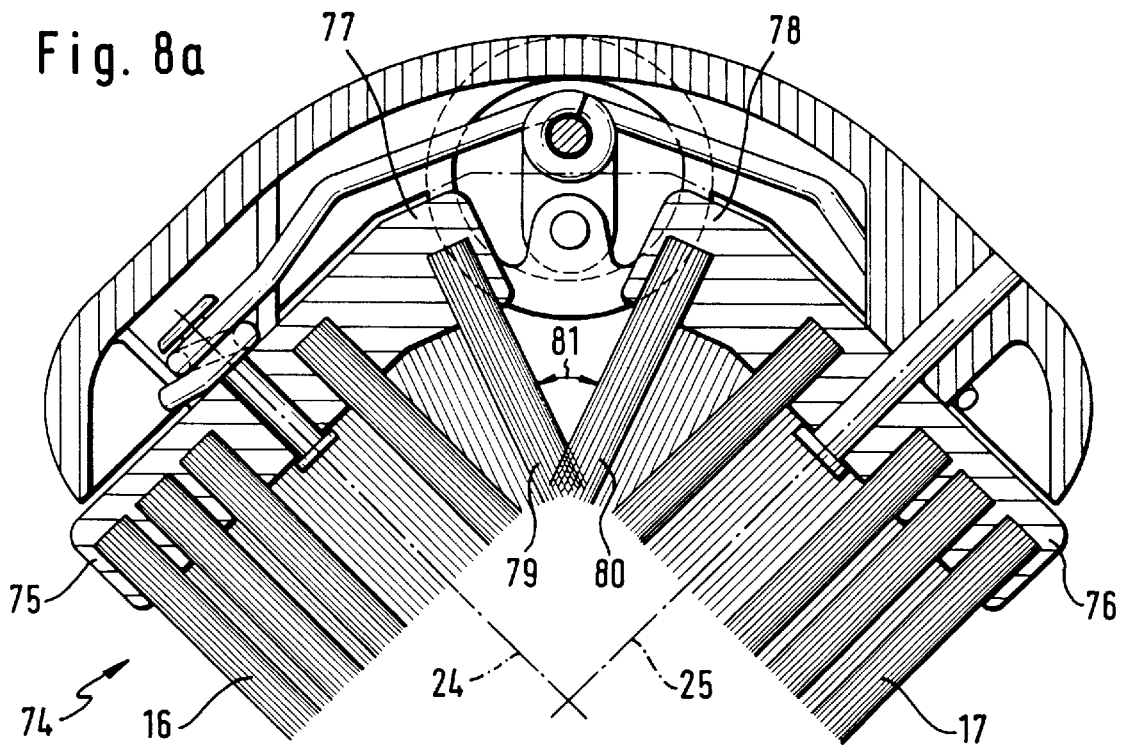
FIG. 8a is a schematic cross sectional view of a brush section for an electric toothbrush utilizing a sixth embodiment, taken along a plane corresponding to the plane 2a—2a of FIG. 1.

FIG. 8a illustrates a brush section 74 having two bristle carriers 75, 76 including each an oval bulge 77 and 78, respectively. The bulges 77, 78 of the two bristle carriers 75, 76 face each other. In the region of the two bulges 77, 78 the two bristle carriers 75, 76 are of a slightly angled configuration. In the non-angled region of the bristle carriers 75, 76 the bristles 16, 17 are arranged approximately parallel to the respective brush axis 24, 25. By contrast, in the angled region of the bristle carriers 75, 76 bristles 79, 80 are provided which define between them an angle 81 smaller than the angle included by the brush axes 24, 25.

Figure 8B:
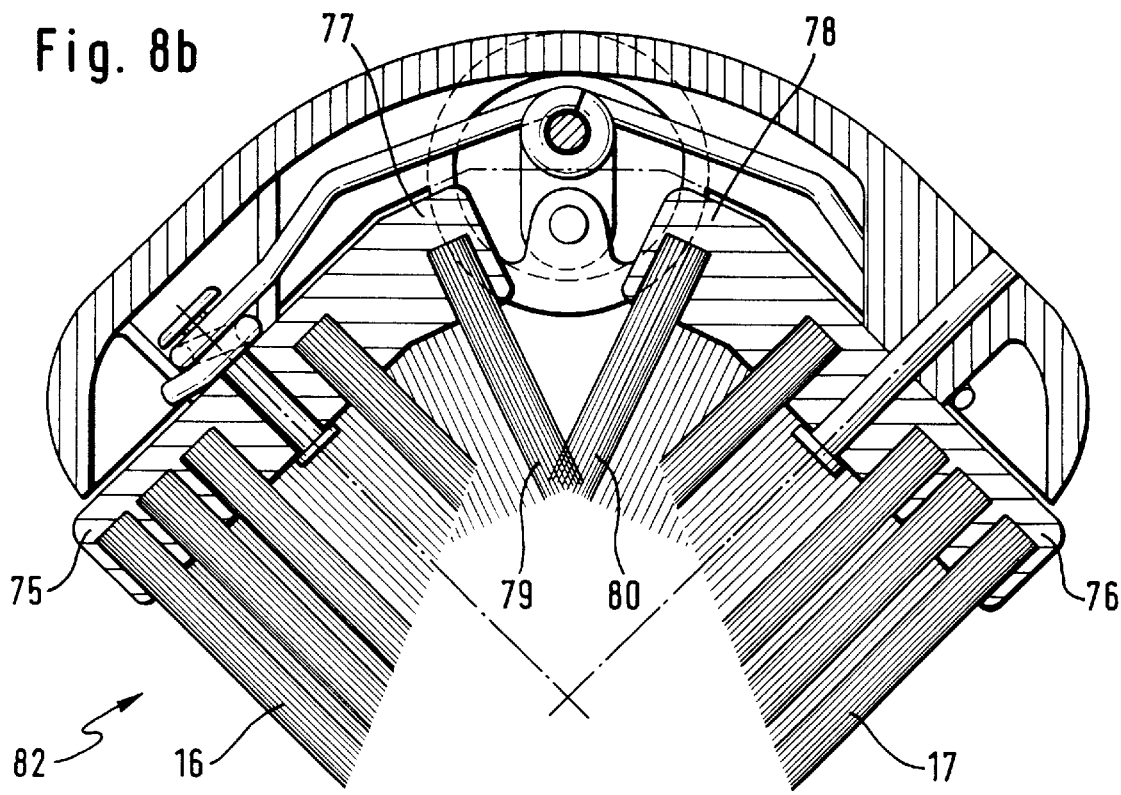
FIG. 8b is a schematic cross sectional view of a brush section for an electric toothbrush utilizing a seventh embodiment, taken along a plane corresponding to the plane 2a—2a of FIG. 1.

FIG. 8b illustrates a brush section 82 which, in contrast to the brush section 74 explained in the foregoing with reference to FIG. 8a, has bristles 16, 17 of different length in the non-angled region of the bristle carriers 75, 76. In this embodiment, the bristles 16, 17 have their maximum length on the side remote from the facing bulges 77, 78 of the bristle carriers 75, 76, their minimum length being on the side of the bristle carriers 75, 76 close to the bulges 77, 78. The length variation of the bristles 16, 17 is approximately linear. The length of the bristles 79, 80 in the angled region of the bristle carriers 75, 76 is approximately between the shortest and the longest length of the bristles 16, 17 in the non-angled region of the bristle carriers 75, 76.

Figure 9A:
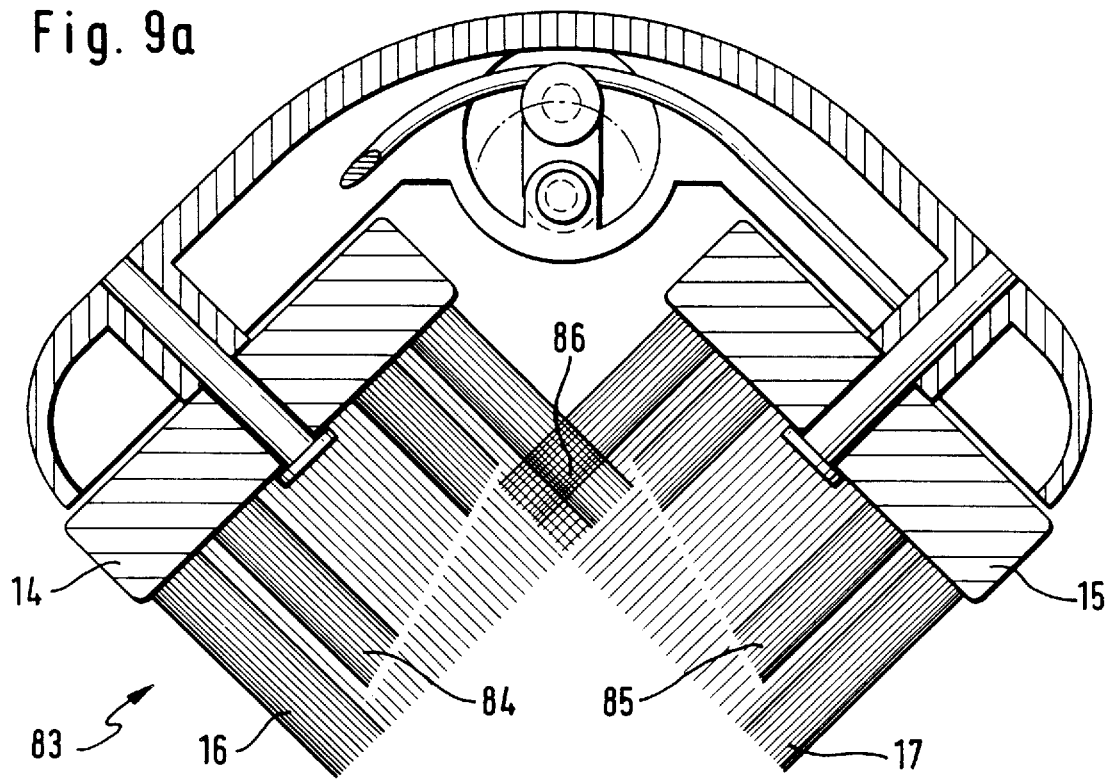
FIG. 9a is a schematic cross sectional view of a brush section for an electric toothbrush utilizing an eighth embodiment, taken along a plane corresponding to the plane 2a—2a of FIG. 1.

FIG. 9a illustrates a brush section 83 in which the bristles 16, 17 extending from the disk-shaped bristle carriers 14, 15 are of equal length only in the region of an outer circular ring. Inside the circular ring bristles 84, 85 of different length are arranged. Departing from an overlap area 86, the length of these bristles 84, 85 increases progressively in outward direction. The overlap area 86 is the area in which the bristles 16, 17 of the two bristle carriers 14, 15 face each other, some of them being in relative engagement. The length variation of the bristles 84, 85 from the inside to the outside is approximately linear.

Figure 9B:
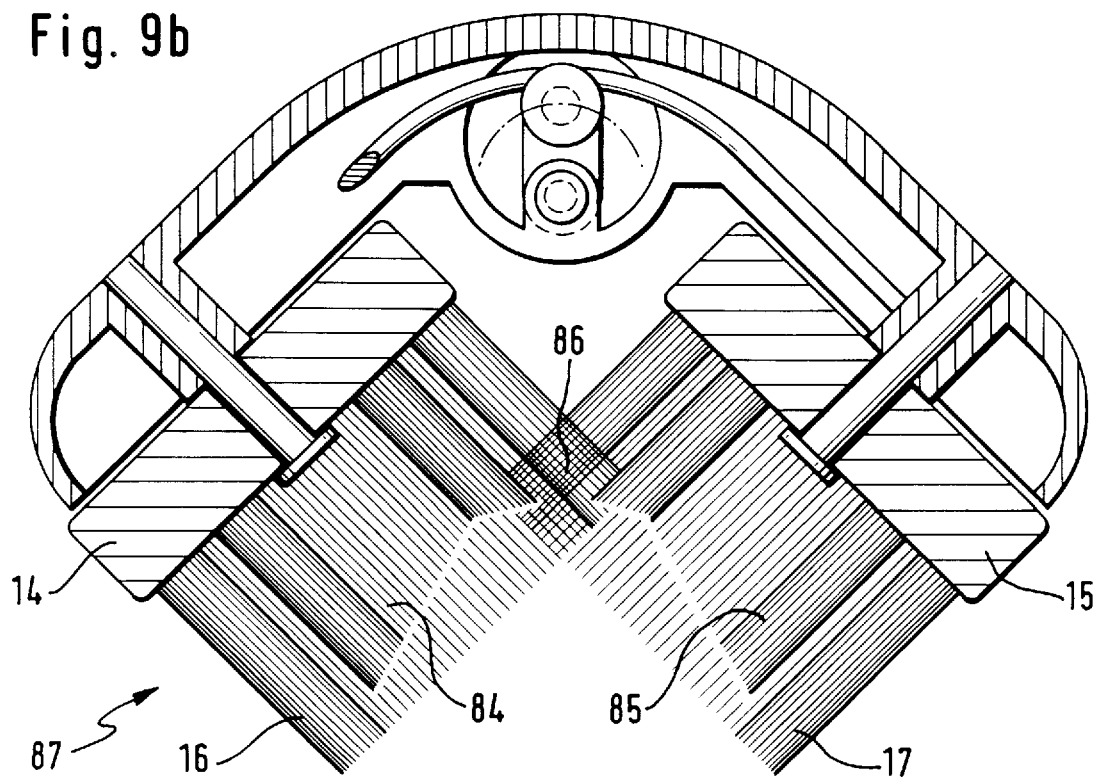
FIG. 9b is a schematic cross sectional view of a brush section for an electric toothbrush utilizing a ninth embodiment, taken along a plane corresponding to the plane 2a—2a of FIG. 1.

FIG. 9b illustrates a brush section 87 in which, in contrast to the brush section 83 explained in the foregoing with reference to FIG. 9a, departing from the overlap area 86 the length of the bristles 84, 85 inside the circular ring referred to first decreases and then increases again.

What is claimed is:

1. A brush section for an electric toothbrush comprising:
   a driver;
   a mounting tube in which the driver is arranged along a longitudinal axis defined by the mounting tube;
   a first bristle carrier mounted for rotation about a first brush axis, and a second bristle carrier mounted for rotation about a second brush axis; and
   a coupling mechanism to effect coupling engagement of the driver with the first and second bristle carriers, such that a motion of the driver effects a rotary motion of the first bristle carrier about the first brush axis and the second bristle carrier about the second brush axis, wherein the first and second brush axes define an approximately right angle therebetween.

2. The brush section as claimed in patent claim 1, wherein the driver is a shaft.

3. The brush section as claimed in patent claim 1, wherein the driver is a rod.

4. The brush section as claimed, in patent claim 2, further comprising first and second connecting rods, wherein the shaft is mounted to oscillate about the longitudinal axis, and wherein the shaft and the first and second bristle carriers are in coupling engagement with one another by the first and second connecting rods.

5. The brush section as claimed in claim 4, wherein each of the first and second connecting rods is connected with the shaft at a location outside the longitudinal axis, the first connecting rod being connected to the first bristle carrier at a location outside the first brush axis, and the second connecting rod being connected to the second bristle carrier at a location outside the second brush axis.

6. The brush section as claimed in claim 4, wherein a first pin extends from the shaft approximately parallel to the longitudinal axis, a second pin extends from the first bristle carrier approximately parallel to the first brush axis, and a third pin extends from the second bristle carrier approximately parallel to the second brush axis, the first connecting rod defining a first eye and a second eye, and the second connecting rod defining a third eye and a fourth eye, the first pin being positioned in the first eye of the first connecting rod and the third eye of the second connecting rod, the second pin being positioned in the second eye of the first connecting rod, and the third pin being positioned in the fourth eye of the second connecting rod.

7. The brush section as claimed in claim 3, wherein the rod is displaceable in the direction of the longitudinal axis and is adapted to oscillate, the rod and the first and second bristle carriers being in coupling engagement with each other by a first and a second connecting rod.

8. The brush section as claimed in claim 7, wherein each of the first and second connecting rods is connected with the rod at a first end of the respective connecting rod, the first connecting rod being connected to the first bristle carrier at a location outside the first brush axis at a second end of the first connecting rod, the second connecting rod being connected to the second bristle carrier at a location outside the second brush axis at a second end of the second connecting rod.

9. The brush section as claimed in claim 7, wherein a first pin extends from the rod approximately transversely to the longitudinal axis, a second pin extends from the first bristle carrier approximately parallel to the first brush axis, and a third pin extends from the second bristle carrier approximately parallel to the second brush axis, the first connecting rod defining a first eye and a second eye, and the second connecting rod defining a third eye and a fourth eye, the first pin being positioned in the first eye of the first connecting rod and the third eye of the second connecting rod, the second pin being positioned in the second eye of the first connecting rod, and the third pin being positioned in the fourth eye of the second connecting rod.

10. The brush section as claimed in claims 6 or 9, wherein the eyes and pins have sufficient relative clearance for spatial movement.

11. The brush section as claimed in claims 4 or 7, wherein the first and second connecting rods are fabricated from a bent piece of round metal.

12. The brush section as claimed in claim 3, wherein the rod is displaceable in the direction of the longitudinal axis and is adapted to oscillate, the rod and the first and second bristle carriers being in coupling engagement with each other by a transverse rod.

13. The brush section as claimed in claim 12, wherein the rod is fixedly connected with the transverse rod, a first pin extends from the first bristle carrier approximately parallel to the first brush axis and a second pin extends from the second bristle carrier, approximately parallel to the second brush axis, the transverse rod defining a first slot at a first end of the transverse rod and a second slot at a second end of the transverse rod, the first pin being positioned in the first slot and the second pin being positioned in the second slot.

14. The brush section as claimed in claim 2, wherein the first bristle carrier is affixed to a first arm and the second bristle is affixed to a second arm, the arms being arranged so as to be pivotal about a pivot axis disposed approximately parallel to the longitudinal axis.

15. The brush section as claimed in claim 2, further comprising first and second arms, wherein the first bristle carrier is affixed to the first arm and the second bristle carrier is affixed to the second arm, the arms being arranged so as to be pivotal about the longitudinal axis.

16. The brush section as claimed in claim 14 or 15, wherein the shaft and the first and second arms are mounted on a bearing pin.

17. The brush section as claimed in claim 1, further comprising a spring which exerts a force on the first and second bristle carriers in the direction of an initial position.

18. The brush section as claimed in claim 1, wherein each of the first and second bristle carriers have an oval bulge.

19. The brush section as claimed in claim 18, wherein the oval bulges are arranged so that the oval bulge of the first bristle carrier faces the oval bulge of the second bristle carrier.

20. The brush section as claimed in claim 1, further comprising a first multiplicity of bristles which extend from the first bristle carrier and a second multiplicity of bristles which extend from the second bristle carrier, a first portion of the first multiplicity of bristles and a first portion of the second multiplicity of bristles defining an included angle therebetween.

21. The brush section as claimed in claim 20, wherein said first portion of said first multiplicity of bristles and said first portion of said second multiplicity of bristles define an acute angle therebetween, the first multiplicity of bristles having a second portion of bristles being aligned approximately parallel to the first brush axis and the second multiplicity of bristles having a second portion of bristles being aligned approximately parallel to the second brush axis.

22. The brush section as claimed in claim 21, wherein the bristles extending from each of the two bristle carriers differ in length.

23. The brush section as claimed in claim 22, wherein the length of the bristles extending from each of the two bristle carriers increase progressively as the relative distance between the first multiplicity of bristles and the second multiplicity of bristles becomes greater.

* * * * *